United States Patent [19]

Stampfer et al.

[11] 4,423,145

[45] Dec. 27, 1983

[54] ENHANCED GROWTH MEDIUM AND METHOD FOR CULTURING HUMAN MAMMARY EPITHELIAL CELLS

[76] Inventors: Martha R. Stampfer, 7290 Sayre Dr.; Helene S. Smith, 5693 Cabot Dr., both of Oakland, Calif. 94611; Adeline J. Hackett, 82 Evergreen Dr., Orinda, Calif. 94563

[21] Appl. No.: 261,086

[22] Filed: May 7, 1981

[51] Int. Cl.$^3$ .................... C12Q 1/18; C12N 5/00; C12R 1/91

[52] U.S. Cl. .................................. 435/32; 435/240; 435/948

[58] Field of Search ............... 435/29, 240, 241, 32, 435/201, 219, 267, 948; 23/230 B; 436/64, 65

[56] References Cited

PUBLICATIONS

Armstron et al.; "Co-Cultivation of Human Primary Breast Carcinomas", Cancer Research 38: 984–998, (1978).
Yang et al.; "Effects of Hormones . . . "; Cancer Research 41: 1021–1027, (1981).
Taylor-Papadimitriou et al.; "Growth Requirements . . . "; Int. J. Cancer 20: 903–908, (1977).
Kirkland et al., "Growth of Normal and Malignant . . . "; J. of Nat. Cancer Inst. 63: 29–42, (1979).
The Merck Index, 8th Edition, (1968), p. 75.
Stampfer et al., "Growth of Human Mammary Epithelium in Culture and Expression of Tumor-Specific Properties", Cold Spring Harbor Conferences on Cell Proliferation, vol. 9, Sep. 1–6, 1981, pp. 819–829.
Prop et al., "Sequential Enzyme Treatment of Mouse Mammary Gland", Tissue Culture Methods and Applications, by Kruse et al., (1973).
Taylor-Papadimitriou et al., "Some Properties of Cells Cultured from Early Lactation Human Milk", Journal of the National Cancer Institute, 56(6), (1977), pp. 1563–1568.
Flaxman, "In Vitro Studies of the Human Mammary Gland: Effects of Hormones on Proliferation in Primary Cell Cultures", Journal of Investigative Dermatology, 61(2), (1973), pp. 67–71.
Buehring, "Culture of Human Mammary Epithelial Cells: Keeping Abreast With a New Method", Journal of the National Cancer Institute, 49, (1972), pp. 1433–1434.
Yang et al., "Primary Culture of Human Epithelial Cells Embedded in Collagen Gels", Journal of the National Cancer Institute: 65(2), (8–1980), pp. 337–343.
Litwin, "A Survey of Various Media and Growth Factors Used in Cell Cultivation", Developments in Biological Standards, 42, pp. 37–45, (1978).
Jakoby et al., Cell Culture Methods in Enzymology, 58, (1979), pp. 92, 99, 153, 358, 359, 567.
Yang et al., "Sustained Growth in Primary Culture of Normal Mammary Epithelial Cells Embedded in Collagen Gells," Proceedings of the National Academy of Sciences, 77(4), (4–1980), pp. 2088–2092.
Rothblat et al., "Growth, Nutrition and Metabolism of Cells in Culture", vol. II, Academic Press, NY, pp. 224–225, (1972).
Hamburger et al.; "Primary Bioassay of Human Tumor Stem Cells"; Science 197: 461–463, (1977).
Salmon et al.; "Quantification of Differential Sensitivity . . . "; New England Jo. of Med. 298: 1321–1327, (1978).
Sandback et al.; "Assay of Clonogenic Cells . . . "; Proc. Am. Ass'n. of Cancer Research 71: 139, (1980).

Primary Examiner—Thomas G. Wiseman
Assistant Examiner—John E. Tarcza
Attorney, Agent, or Firm—Townsend & Townsend

[57] ABSTRACT

Methods are disclosed for isolating and culturing human mammary epithelial cells of both normal and malignant origin. Tissue samples are digested with a mixture including the enzymes collagenase and hyaluronidase to produce clumps of cells substantially free from stroma and other undesired cellular material. Growing the clumps of cells in mass culture in an enriched medium containing particular growth factors allows for active cell proliferation and subculture. Clonal culture having plating efficiencies of up to 40% or greater may be obtained using individual cells derived from the mass culture by plating the cells on appropriate substrates in the enriched media. The clonal growth of cells so obtained is suitable for a quantitative assessment of the cytotoxicity of particular treatment. An exemplary assay for assessing the cytotoxicity of the drug adriamycin is presented.

14 Claims, No Drawings

ENHANCED GROWTH MEDIUM AND METHOD FOR CULTURING HUMAN MAMMARY EPITHELIAL CELLS

BACKGROUND OF THE INVENTION

1. Field of the Invention

The present invention relates generally to the field of cytology, and more particularly, it relates to an enhanced growth medium and method for isolating human mammary epithelial cells and growing such cells in both mass and clonal culture.

2. Description of the Prior Art

Studies on the cellular physiology of normal and pathologic human mammary epithelium have been hampered by the difficulty of growing these cells in vitro, free from other cellular elements of the mammary gland. While the short-term culture of epithelial cells derived from lactation fluids, reduction mammoplasties, benign tumors, non-tumor mastectomy tissue and primary carcinomas is known, in all cases the cells have displayed very limited potential for continued cell division and inability to maintain active cell growth upon serial subculture.

It would be particularly useful to be able to grow normal and malignant human mammary epithelial cells in both mass and clonal culture. For mass culture, it would be desirable to be able to increase the potential for cell division to be able to serially subculture cells from all specimens obtained, and to be able to cryopreserve cells from each individual donor for repetition of experiments. Such a cell culture system can be used for studies to develop an understanding of the physiology of normal and malignant human mammary epithelial cells and what agents might be capable of inducing normal cells to exhibit the properties of malignant cells.

A clonal culture where a small number of cells are plated and remain separate so that the percentage of individual cells that proliferate can be determined, may be used in a clonal assay to measure in vitro the cytotoxicity of particular noxious agents such as chemicals, chemotherapy drugs, radiation and the like. A clonal assay for human tumor cells was reported by Hamburger, et al., in an article entitled "Primary Bioassay of Human Tumor Stem Cells" *SCIENCE* 197: 461–463 (1977). In that procedure, individual cells suspended in agar enriched medium were plated into a petri dish having an agar feeder layer. While functional, this method suffers from several disadvantages. First, the plating efficiency is often lower than one colony per 10,000 cells plated. Second, there are difficulties in obtaining single cell suspensions, particularly with scirrhus tumors. Third, cryopreservation of primary tumor tissue has proven difficult. A clonal assay for measuring cytotoxicity of chemotherapeutic drugs is described in the paper "Quantitation of Differential Sensitivity Of Human-Tumor Stem Cells to Anticancer Drugs" by Salmon, et al., in the *NEW ENGLAND JOURNAL OF MEDICINE*, 298:1321–1327 (1978). The procedure described therein tested tumor cells from patients with myelomas and ovarian carcinomas for cytotoxic response for various chemotherapeutic drugs.

The most successful attempt at clonal growth of human mammary epithetal cells heretofore was reported by Sandback et al., in an article entitled "Assay for Clonogenetic Cells in a Human Breast Cancer" *PROCEEDINGS AM. ASSOC. CANCER RES.* 71:139 (1980) (using agar); and by Yang et al., "Effects of Hormones and Growth Factors on Human Mammary Epithelial cells on Collagen Gell Culture" *CANCER RES.* 41:1021–27 (1981) (using a collagen matrix). However, clonal growth was not obtained with either method unless more than $10^5$ cells were plated per dish.

There have been other reports of human mammary epithelial growth stimulated by feeder layers of fibroblastic (mouse and human) or bovine lens epithelial cells. See, Taylor-Papadimitriou, et al., "Growth Requirements of Human Mammary Epithelial Cells in Culture" *INT. J. CANCER* 20:903–908; and Kirkland, et al., "Growth of Normal and Malignant Human Mammary Epithelial Cells In Culture" *JOURNAL OF THE NATIONAL CANCER INSTITUTE* 63:29–42. Feeder layers formed from mouse or human mesenchymal cells are reported in Armstrong, et al., "Co-Cultivation Of Human Primary Breast Carcinomas In Embrionic Mesenchyme Resulting In Growth And Maintenance of Tumor Cells" *CANCER RESEARCH* 38:894–898. The use of such feeder layers in the absence of an adequate growth medium has not been able to extend the growth potential of pure cultures of human mammary epithelium to the extent desired.

SUMMARY OF THE INVENTION

The present invention provides an enhanced growth medium for culturing human mammary epithelial cells. The growth medium incudes growth factors obtained from conditioned medium which yield reproducibly active epithelial cell growth for extended periods in culture and allow serial subculture.

The method of the present invention includes isolating the mammary epithelial cells into viable clumps to obtain large quantities of relatively pure mammary epithelial cells from human mammary tissue, and mass culturing these clumps of cells in the enhanced growth medium. Such isolation is achieved with a particular enzyme digestion mixture including collagenase and, preferably, collagenase and hyaluronidase. After the mass culture is established, individual cells may be separated and transferred to a second culture including the enhanced medium and a fibroblast feeder layer where clonal growth may be established from the individual cells. By mass culturing the cells in clumps, the viability of the cells is established prior to plating the cells individually in clonal culture, resulting in very high plating efficiencies.

DESCRIPTION OF THE PREFERRED EMBODIMENT

The method of the present invention involves three related techniques or steps, which, when performed together, allow the mass and clonal culture of human mammary epithelial cells. The method is particularly useful to study the cytotoxic, carcinogenic, and general physiological effects of various agents on human mammary epithelial cells. The first step involves the isolation of epithelial clumps (both normal and malignant) from samples of mammary tissue, typically obtained from reduction mammoplasties and mastectomies or other surgical techniques, by the use of specific enzymes to digest the tissue into clumps which are then separated from dissociated stromal cells, myoephithelial cells, and other mammary cellular material by filtration. The second step involves plating the clumps in mass culture to allow extensive proliferation free from contaminating stromal cells and other material. The final step involves the separation of individual cells from the mass culture and the transfer of these cells into a clonal cluture where colonies proliferate from the individual cells.

The mass culture resulting from the first two steps of this method provides a sufficient growth of mammary epithelial cells in itself for many biochemical assays. Moreover, the culture medium used in the method allows the serial subculturing of the cells and provides viable cells which may be frozen and stored. Each of these steps will now be described in greater detail.

1. Isolation of Epithelial Clumps

Samples of human mammary tissue collected during surgery are stored at low temperature (typically 4° C.) for up to 72 hours in a conventional storage medium. The tissue is prepared for separation of epithelial from stromal components by first removing skin and grossly fatty areas and gently lacerating the remaining tissue with opposing scapels.

The tissue is then exposed to an enzyme digestion mixture including collagenase and more preferably, collagenase and hyaluronidase. The collagenase in the enzyme mixture serves to break down the stroma, while the hyaluronidase digests the basement membrane, producing orginoid structures containing epithelial and myoepithelial cells. The formula for the digestion mixture is as follows.

| ENZYME DIGESTION MIXTURE | | |
|---|---|---|
| | Concentration[1] | |
| Component | Effective Range | Preferred Range |
| Collagenase | 50-500 U/ml | 150-250 U/ml |
| Hyaluranidase | 0-250 U/ml | 80-120 U/ml |
| Insulin | 0-20 µg/ml | 5-15 µg/ml |
| Serum (FBS) | 1-20% | 5-15% |

[1]Present in basal medium, e.g., Ham's F-12 or Dulbecco's Minimal Essential Medium. The mixture further includes sufficient antibiotic, typically a combination of penicillin, streptomycin, Fungizone ®, (amphotericin B) and the like, to inhibit the growth of contaminants.

The enzymatic digestion preferably proceeds at an elevated temperature in the range from approximately 20° C. to 37° C. with gentle agitation and is stopped when clumps of these cells with ductal, alvolar and ductal-alvolar like structures are observed to be free from attached stromal elements. The suspension is then filtered through uniform pore-size filters (e.g., polyester or nylon) to remove undesired cellular components. After filtering, the cells and the filtrate are centrifuged to separate the cells which are then resuspended into cell preservative medium. The cells in medium may be stored in aliquots which can be frozen and stored in liquid nitrogen. The cells have been stored frozen for two years with no apparent reduction in viability.

2. Mass Culturing Procedures

Mammary epithelial cells which have been prepared according to the above procedure can be used either fresh or after freezing according to the following procedure. The cells are transferred to suitable containers, such as plastic petri dishes or flasks, maintained at 37° C. in a humidified $CO_2$ incubator. The containers hold growth medium which includes a conventional basal growth medium supplemented by particular growth factors, as described more fully hereinafter. The medium is changed every 48 to 72 hours.

The addition of the growth factors to the basal medium enhances the viability of human mammary epithelial cells in in vitro culture. The growth factor, which is as yet unidentified, is obtained from conditioned medium (CM) from certain specific human cell lines. CM from human fetal intestine epithelial cell line Hs74Int and from human bladder epithelial cell line Hs767Bl provide the essential growth factor. CM from human myoepithelial cell line HS578Bst appears to enhance cell attachment, but does not provide the essential growth factor. These cell lines are available from the Cell Culture Laboratory, University of California, School of Public Health, Oakland, Calif., where they are designated HS0074, HS0767 and HS0578, respectively. CM is obtained from subconfluent and confluent populations of these cell lines by collecting the supernatant fluid every 2 to 4 days. The fluid is filtered and either used immediately or stored at −20° C.

The approximate effective and preferred compositions of the growth media are as follows:

| ENHANCED GROWTH MEDIA | | |
|---|---|---|
| | Concentration in Basal Media[1] | |
| Component | Effective Range | Preferred Range |
| Insulin | 0.1-20 µg/ml | 5-10 µg/ml |
| Hydrocortisone | 0-10 µg/ml | 0.05-0.15 µg/ml |
| Epidermal Growth Factor | 0-20 ng/ml | 3-8 ng/ml |
| 74Int CM[2] | 10-50% | 25-35% |
| 767B1 CM[2] | 10-50% | 25-35% |
| 578Bst CM | 0-20% | 5-15% |
| Estradiol | $0-10^{-7}M$ | approximately $10^{-9}M$ |
| Triiodothyronine | $0-10^{-7}M$ | approximately $10^{-8}M$ |
| Cholera Toxin | 0.1-1000/ng/ml | 1-10 ng/ml |
| Serum | 0-3% | 0.2-0.7% |

[1]The basal medium is a conventional minimal essential medium such as Ham's F-12 or Dulbecco's Minimal Essential Medium.
[2]The concentrations of both 74Int and 767B1 are additive. The desired concentration may be provided by either 74Int CM or 767B1 CM alone, or in combination.

Cells are subcultured by known methods i.e., total medium is removed and, after washing, the cells are partially trypsinized with a mixture of saline, trypsin and Versene ® (STV) described in Owens, et al. (1974) JNCI 53:261 until the desired percentage of cells have detached from the clumps. The detached cells are added at an appropriate dilution to a suitable container with fresh growth medium, thus allowing serial mass culturing of the epithelial cells.

The percentage of cells which proliferate upon subculture varies depending on the condition of the mass culture from which they are derived. Cells from subconfluent, proliferating cultures are readily passaged, while those from primary cultures which have been allowed to become confluent are not. This is true whether the subculture is to be a mass culture or a clonal culture, as discussed hereinafter.

3. Clonal Growth Of Mammary Epithelial Cells

For clonal growth, a subconfluent mass culture of epithelial cells is trypsinized with STV to detach individual cells from the clump-like growths in the medium. The individual cells are counted, typically in a hemacytometer, and cultured on a substrate, typically a plastic dish. The growth of isolated mammary epithelial cells may be greatly enhanced by plating the substrate with feeder cells, typically normal human skin fibroblast, prior to culturing the epithelial cells. The effect of providing such a layer of feeder cells is summarized for three cell specimens in Table 2.

TABLE 2
Effect of Fibroblast Feeder Cells[1] on Colony Formation

| Cell Specimen[2] | Day Scored | Efficiency of Colony Formation (%) | | |
|---|---|---|---|---|
| | | Fibroblasts | Irradiated Fibroblasts | Without Fibroblasts |
| 1 | 5 | 6 | 6 | 0.95 |
| | 12 | 8 | 8 | 0.25 |
| 2 | 5 | 24 | 27 | 5.1 |
| | 12 | 22 | 21 | 2.5 |
| 3 | 5 | 22 | 22 | 8.3 |
| | 12 | 17 | 27 | 0.96 |

[1]Cell line PH140SK at $5 \times 10^4$ cells per 60 mm dish.
[2]Cell specimens 1 and 2 were obtained from nonmalignant tissue; specimen 3 was obtained from primary carcinoma tissue.

The provision of a fibroblast feeder layer appeared to have two effects. First, the plating efficiency was greatly increased over that observed without such provision. Second, the growth of the individual colonies continued over a longer period. Without fibroblasts, colonies contained fewer cells and continued growth beyond five days in culture was sparse.

It is further desirable to irradiate the fibroblast prior to culturing the epithelial cells to inhibit competitive growth of the fibroblast cells to the detriment of epithelial cells. It has been observed that colony growth on irradiated fibroblasts is somewhat larger.

TABLE 3
Success Rate in Culturing Human Mammary Epithelial Cells

| | Ratio of Number of Viable Cultures to the Number of Cultures Seeded | |
|---|---|---|
| Source of Tissues | Mass Culture | Colony Assay |
| Nonmalignant Tissues[1] | 14/15 | 10/10 |
| Primary Carcinomas | 9/10 | 9/9 |
| Metastases | | |
| to hypodermis | 2/3 | 1/1 |
| to vagina | 1/1 | 1/1 |
| to contralateral breast extending from upper arm | 1/1 | 1/1 |
| to lymph node | 0/3 | — |
| to pleura | 1/2 | 0/1 |

[1]Reduction mammoplasties and mastectomy tissue peripheral to carcinomas.

Table 3 summarizes the success rate in culturing human mammary epithelial cells under both clonal and mass culture conditions. Utilizing the media formulation set forth above, over 90% of the cultures obtained from non-malignant tissues, primary carcinomas and hypodermal metastases grew readily in mass culture for at least one passage. In every case tested, the specimens which grew in mass culture also grew in clonal assay. The fact that hypodermal metasteses grew as well as primary carcinomas excluded the possibility that only the non-malignant cells peripheral to the carcinomas were capable of growth in culture.

The growth of the desired mammary epithelial cells was verified by observing the colonies. The cells in culture were identified by their morphological characteristics, specifically their cubiodal shape. Additionally, epithelial cells lack anti-hemophilic factor VIII antigen. Moreover, the primary cultures, when allowed to remain confluent for several weeks form dome-like structures thought characteristic of epithelial cells. Finally, the cells were positive for the human mammary-specific antibody prepared against milk fat globule and showed a distinctive pattern of cell associated fibronectin.

4. Exemplary Assay for Assessing the Cytotoxicity of Particular Agents

Utilizing the clonal assay described hereinabove, an assay may be performed to determine the effect of particular noxious agents such as chemicals, chemotherapy drugs and radiation on mammary epithelial cells. The method comprises growing a clonal culture of the cells obtained by surgical methods according to the proceedure described hereinabove. Then, by administering the agent under consideration to a clonal culture having a known number of proliferating colonies, a quantitative indication of the effect of the agent, e.g., the number of colonies killed, may be obtained.

The particular clonal assay disclosed assesses the cytotoxicity of various chemotherapeutic drugs on malignant cells derived from patients undergoing treatment. For each drug of interest, a number of clonal cultures are prepared so that the drug may be administered at differing concentrations, incuding zero concentration. Moreover, differing numbers of cells are plated to assure viable colony formation regardless of the plating efficiency of the particular cell under examination. It has been found that although plating efficiency for cells varies among individuals, the plating efficiency for mammary epithelial cells from an individual is constant. Thus, by plating a series of cultures, each series having a different initial plating count, clonal cultures having a range of viable colonies can be expected. Such a range is usefull to assess drugs which themselves may display a wide range of effectiveness. The drugs, in solution with growth medium, are added approximately 24 hours after plating. Four hours after administering the drug, the drug-containing medium is removed and all plates are washed with basal salts to assure complete removal of the drug. Each dish is then refed with medium containing additional fibroblasts in case the drug has destroyed the ability of the initial fibroblast layer to feed the epithelial cells. Thereafter, the dishes are periodically refed until readily visualized colonies are present on at least some of the dishes.

The dishes are then fixed with methanol and stained to allow visual assessment of the cell growth at the different drug dosages. Initially, a determination is made of the plating efficiency of the particular tumor cell at zero dosage. Once this is determined, the survival rate at the various positive dosage rates can easily be assessed by comparison with the zero dosage growth. Differing numbers of cells were plated because particular cells with high plating efficiencies will be obscured at high density plating, while those with low plating efficiencies will produce very few colonies at low plating density.

The adriamycin sensitivity of five breast carcinoma specimens from previously untreated donors was assessed using the assay just described. Tumor cells were mass cultured and plated to form colonies from individual stem cells. Individual cells were plated in clonal culture at concentrations of $10^4$, $10^3$ and 200 cells/dish. Varying concentrations of adriamycin, including a zero concentration, were administered to a series of dishes each having identical cell concentrations.

The adriamycin concentration associated with both a 60% survival rate for the colonies and a <0.1% survival rate are tabulated in Table 4. The specimens are listed in order of increasing adriamycin concentration required for 60% survival. Heterogeneity and drug response among the specimens is listed by the fact that the order among the cultures differed between the two survival rates.

TABLE 4

Sensitivity of Cultured Human Mammary Carcinomas to Adriamycin

| Tumor Specimen | Adriamycin Concentration[1] (ng/ml) | |
| --- | --- | --- |
| | 60% Survival | <0.1% Survival |
| 1 | 1.0 | 100 |
| 2 | 1.3 | 250 |
| 3 | 2.0 | 500 |
| 4 | 5.5 | 50 |
| 5 | 15.0 | 5000 |

[1]In solution with growth media.

Although the best mode contemplated for carrying out the present invention has been herein shown and described, it will be apparent that modification and variation may be made by those skilled in the art without departing from what is regarded to be the subject matter of the present invention.

What is claimed is:

1. A method for preparing samples of human mammary tissue to obtain a mass culture of mammary epithelial cells, said method comprising:
    digesting the tissue samples with an enzyme digestion mixture including at least one enzyme selected to break down the mammary tissue into clumps of epithelial cells substantially free from attached stromal cells;
    separating the clumps of epithelial cells from the stromal cells and other cellular material; and,
    culturing the clumps of epithelial cells in a medium including conditioned media obtained from cultures of cells selected from the group consisting of human fetal intestine epithelial cells and human bladder epithelial cells so that the mammary epithelial cells in the clumps proliferate.

2. A method for passaging the epithelial cells obtained by the steps of claim 1 to obtain a clonal culture, said method comprising the additional steps of:
    separating individual cells from the clumps of epithelial cells; and
    plating individual cells onto a substrate in a medium including conditioned media obtained from cultures of cells selected from the group consisting of human fetal intestine epithelial cells and human bladder epithelial cells so that the cells proliferate in isolation from one another to form colonies.

3. An assay for determining the toxicity of a particular agent to human mammary epithelial cells, wherein viable colonies of human mammary epithelial cells are prepared by:
    digesting samples of human mammary tissue with an enzyme digestion mixture including at least one enzyme selected to break down the mammary tissue into clumps of epithelial cells substantially free from attached stromal cells;
    separating the clumps of epithelial cells from the stromal cells and other cellular material; and,
    culturing the clumps of epithelial cells in a medium including conditioned media obtained from cultures of cells selected from the group consisting of human fetal intestine epithelial cells and human bladder epithelial cells so that the cells in the clumps proliferate;
    separating individual cells from the clumps of epithelial cells; and
    plating a relatively small number of the individual cells onto a substrate in a medium including conditioned media from at least one media obtained from human fetal intestine epithelial cells and human bladder epithelial cells so that the cells proliferate in isolation from one another to form colonies;
    said assay comprising:
    exposing the viable colonies to the particular agent; and
    determining the survival rate of the colonies.

4. A method as in claim 1, wherein the step of digesting the tissue is carried out with agitation and at a temperature in the range from approximately 20° to 37° C. and wherein said digestion step is terminated when clumps of the cells are observed to be formed.

5. A method as in claim 2, wherein the step of separating individual cells from the clumps of epithelial cells comprises treating the clumps with a mixture including trypsin.

6. A method as in claim 2, wherein the substrate is plated with feeder cells prior to culturing the epithelial cells.

7. A method as in claim 6, wherein the feeder cells are normal human skin fibroblasts.

8. An assay for determining the toxicity of a particular agent to human mammary epithelial cells, said assay employing a culture of human mammary epithelial cells prepared by:
    digesting samples of human mammary tissue with an enzyme digestion mixture including at least one enzyme selected to break down the mammary tissue into clumps of epithelial cells substantially free from attached stromal cells;
    separating the clumps of epithelial cells from the stromal cells and other cellular material; and
    culturing the clumps of epithelial cells in a medium including conditioned media obtained from cultures of cells selected from the group consisting of human fetal intestine epithelial cells and human bladder epithelial cells so that the cells in the clumps proliferate;
    separating individual cells from the clumps of epithelial cells; and
    plating individual cells onto a substrate in a medium including conditioned media from at least one of the media obtained from human fetal intestine epithelial cells and human bladder epithelial cells so that the cells proliferate in isolation from one another to form colonies, wherein said substrate has been plated with feeder cells prior to culturing the epithelial cells;
    said assay comprising:
    exposing the plated cells to the agent;
    terminating the exposure of the colonies to the treatment;
    providing supplemental growth media further including feeder cells;
    allowing the colonies plated on the substrate to proliferate until it is possible to distinguish those colonies which continue to grow from those colonies which have ceased to grow prior to determining the survival rate; and
    determining the toxicity by comparing the number of viable colonies with the number of colonies which have ceased to grow.

9. A growth medium, comprising insulin, cholera toxin and conditioned medium obtained from a culture of cells selected from the group consisting of human fetal intestine epithelial cells and human bladder epithelial cells, said components being present in basal medium at concentrations effective to promote the growth of human mammary epithelial cells therein.

10. A growth medium, as in claim 9 wherein the insulin is present at a concentration in the range from approximately 0.1 to 20 µg/ml.

11. A growth medium, as in claim 9 wherein the cholera toxin is present at a concentration in the range from approximately 0.1 to 1000 ng/ml.

12. A growth medium, as in claim 9 wherein the conditioned media is present at a concentration in the range from approximately 10 to 50 weight percent.

13. A growth medium, as in claim 9 including additional components selected from the group consisting of epidermal growth factor at a concentration not exceeding approximately 20 ng/ml, triiodothyronine at a concentration not exceeding approximately $10^{-7}$M, estradiol at a concentration not exceeding $10^{-7}$M, and serum not exceeding 3% by weight.

14. A viable culture of human mammary epithetial cells in a basal medium comprising said cells, insulin, cholera toxin and conditioned medium obtained from a culture of cells selected from the group consisting of human fetal instestine epithelial cells and human bladder epithelial cells wherein said insulin, cholera toxin and conditioned medium are present in amounts sufficient to promote the growth of human mammary epithetial cells.

* * * * *